United States Patent
Bulut et al.

(10) Patent No.: US 10,701,210 B2
(45) Date of Patent: Jun. 30, 2020

(54) SYSTEMS AND METHODS FOR MATCHING SUBJECTS WITH CARE CONSULTANTS IN TELENURSING CALL CENTERS

(71) Applicant: KONINKLIJKE PHILIPS N.V., Eindhoven (NL)

(72) Inventors: Murtaza Bulut, Eindhoven (NL); Paul Anthony Shrubsole, Gelderland (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/086,462

(22) PCT Filed: Mar. 23, 2017

(86) PCT No.: PCT/EP2017/056959
§ 371 (c)(1),
(2) Date: Sep. 19, 2018

(87) PCT Pub. No.: WO2017/162808
PCT Pub. Date: Sep. 28, 2017

(65) Prior Publication Data
US 2019/0109947 A1 Apr. 11, 2019

Related U.S. Application Data

(60) Provisional application No. 62/311,988, filed on Mar. 23, 2016.

(51) Int. Cl.
*H04M 3/00* (2006.01)
*H04M 3/58* (2006.01)
(Continued)

(52) U.S. Cl.
CPC ........ *H04M 3/58* (2013.01); *G06Q 10/06311* (2013.01); *G16H 40/20* (2018.01); *G16H 80/00* (2018.01); *H04M 2203/407* (2013.01)

(58) Field of Classification Search
CPC .................. H04M 3/58; G16H 40/20
(Continued)

(56) References Cited

U.S. PATENT DOCUMENTS

| 7,027,621 B1 * | 4/2006 | Prokoski | G06K 9/00248 180/272 |
| 7,184,540 B2 * | 2/2007 | Dezonno | H04M 3/523 379/265.02 |

(Continued)

FOREIGN PATENT DOCUMENTS

| EP | 2924635 A1 | 9/2015 |
| WO | 2015160643 A1 | 10/2015 |

OTHER PUBLICATIONS

Wiley-Blackwell, "Telenurses face conflict between what is best for patients and what services are available", ScienceDaily, Feb. 17, 2010, <www.sciencedaily.com/releases/2010/02/100217131206.htm>.

(Continued)

*Primary Examiner* — William J Deane, Jr.

(57) ABSTRACT

The present disclosure relates to a system and method configured for matching subjects that call into a call center where calls are answered by care consultants that provide health care or consult on health care remotely via the call center, wherein the matching is based on holistic information related to both the individual subjects and the individual care consultants. The method being performed by one or more hardware processors configured by machine-readable instructions, the method comprising responsive to receiving a call from a first subject, obtaining first subject information associated with the first subject, obtaining care consultant information associated with a plurality of care consultants associated with the call center including first care consultant information associated with a first care consultant, and analyzing the first subject information and the first care (Continued)

consultant information to determine whether a match exists between the first subject and the first care consultant.

21 Claims, 3 Drawing Sheets

(51) Int. Cl.
*G06Q 10/06* (2012.01)
*G16H 40/20* (2018.01)
*G16H 80/00* (2018.01)

(58) Field of Classification Search
USPC ....... 379/265.01–265.14, 266.01–266.1, 309
See application file for complete search history.

(56) References Cited

U.S. PATENT DOCUMENTS

| | | | | |
|---|---|---|---|---|
| 8,027,455 | B2* | 9/2011 | Moody | H04M 3/42093 379/257 |
| 8,164,461 | B2* | 4/2012 | Bischoff | G06F 19/3418 340/573.1 |
| 8,494,507 | B1* | 7/2013 | Tedesco | A61F 4/00 434/112 |
| 8,515,777 | B1 | 8/2013 | Rajasenan | |
| 9,602,669 | B1* | 3/2017 | Griffith | H04M 3/5175 |
| 10,489,838 | B2* | 11/2019 | Johansson | G06Q 30/0613 |
| 2004/0101127 | A1* | 5/2004 | Dezonno | H04M 3/523 379/265.02 |
| 2005/0163302 | A1* | 7/2005 | Mock | A61B 5/165 379/211.02 |
| 2008/0001735 | A1* | 1/2008 | Tran | G06F 19/3418 340/539.22 |
| 2008/0161733 | A1* | 7/2008 | Einav | A61H 1/0274 601/34 |
| 2008/0165017 | A1* | 7/2008 | Schwartz | A61B 5/0002 340/573.1 |
| 2008/0214903 | A1* | 9/2008 | Orbach | A61B 5/486 600/301 |
| 2010/0254527 | A1* | 10/2010 | Addair | H04M 3/5233 379/265.12 |
| 2011/0125063 | A1* | 5/2011 | Shalon | A61B 5/0006 600/590 |
| 2012/0259649 | A1 | 10/2012 | Mallon et al. | |
| 2013/0051545 | A1* | 2/2013 | Ross | H04M 3/523 379/265.02 |
| 2013/0231574 | A1* | 9/2013 | Tran | A61B 5/0022 600/479 |
| 2014/0051940 | A1* | 2/2014 | Messerschmidt | A61B 5/6803 600/301 |
| 2014/0072136 | A1* | 3/2014 | Tenenbaum | G08B 21/06 381/74 |
| 2014/0140497 | A1* | 5/2014 | Ripa | H04M 3/5133 379/265.06 |
| 2014/0188457 | A1* | 7/2014 | Fink | G06F 17/2785 704/9 |
| 2014/0188459 | A1* | 7/2014 | Fink | G06F 17/2785 704/9 |
| 2014/0330655 | A1* | 11/2014 | Aziz | G06Q 20/40145 705/16 |
| 2015/0141789 | A1* | 5/2015 | Knight | A61B 5/165 600/383 |
| 2015/0256676 | A1* | 9/2015 | Famous | H04M 3/42068 379/265.09 |
| 2016/0135736 | A1* | 5/2016 | Bowers | A61B 5/4833 704/270 |
| 2017/0236176 | A1* | 8/2017 | Johansson | G06Q 10/06311 705/7.13 |
| 2018/0096271 | A1* | 4/2018 | Raanani | G06Q 10/0635 |
| 2018/0181561 | A1* | 6/2018 | Raanani | G06F 17/2785 |

OTHER PUBLICATIONS

Sir, Mustafa et al., "Nurse-patient assignment models considering patient acuity metrics and nurses' perceived workload", Journal of Biomedical Informatics, 55 (2015) 237-248.

Curley, Martha, "Patient-nurse synergy: Optimizing patients' outcomes", American Journal of Critical Care, Jan. 1998, vol. 7, No. 1.

Acar, Ilgin, "A Decision Model for Nurse-to-Patient Assignment", Western Michigan University, May 2010.

Westra, Bonnie, "Telenursing and Remote Access Telehealth", Nursing Informatics Deep Dive, San Francisco, 2012.

"Hospital Hygiene: The Continuing Challenge", International Hospital Equipment and Solutions, vol. 34, Issue 7, Dec. 2008-Jan. 2009.

* cited by examiner

SYSTEMS AND METHODS FOR MATCHING SUBJECTS WITH CARE CONSULTANTS IN TELENURSING CALL CENTERS

CROSS-REFERENCE TO PRIOR APPLICATIONS

This application is the U.S. National Phase application under 35 U.S.C. § 371 of International Application No. PCT/EP2017/056959, filed on 23 Mar. 2017, which claims the benefit of U.S. Provisional Patent Application No. 62/311,988, filed on 23 Mar. 2016. These applications are hereby incorporated by reference herein.

BACKGROUND OF THE INVENTION

1. Field of the Invention

The present disclosure relates to systems and methods for matching subjects that call into a call center where calls are answered by care consultants that provide health care or consult on health care remotely via the call center, wherein the matching is based on holistic information related to both the individual subjects and the individual care consultants.

2. Description of the Related Art

Telenursing (i.e., telephone-based nursing) is becoming an increasingly popular industry due to the availability of various communication channels. It is expected by many that telenursing will be a standard practice in the near future. Telenursing is one way of managing limited resources in healthcare. It is cost efficient, timesaving, and increases a subject's ability to self-care. In many Western countries, telenursing is an expanding part of healthcare. Telenursing work can be complex and knowledge-intensive. Tele-nurses in a call center that provide telenursing are in limited number and have to communicate with many subjects. Tele-nurses may have to work long hours without proper break, resulting in both emotional and physical stress that is likely to influence the quality of communication and support they can provide to the subject.

Currently, the selection of tele-nurse is typically done based on availability, meaning that the subject calling into the call center is connected to the next tele-nurse that is available with no regard for specialty areas of practice. Otherwise, if a subject wants to speak with a tele-nurse specifically versed in the subject's area of need, the subject may have to explain their problems, symptoms, and needs to several people and endure an additional wait time before being manually transferred to a fitting tele-nurse.

SUMMARY OF THE INVENTION

Accordingly, it is an object of one or more embodiments of the present disclosure to provide a system configured for matching subjects that call into a call center where calls are answered by care consultants that provide health care or consult on health care remotely via the call center. Matching is based on holistic information related to both the individual subjects and the individual care consultants. The system comprises one or more hardware processors and/or other components. The one or more hardware processors are configured by machine-readable instructions to, responsive to receiving a call from a first subject, obtain first subject information associated with the first subject. The first subject information includes subject profile information associated with the first subject. The first subject information includes subject conversation characteristics associated with the first subject during a current conversation or a past conversation. The first subject information includes subject previous session information associated with the first subject. The first subject information includes subject real-time physiological state information associated with the first subject. The first subject information includes subject present living conditions information associated with the first subject. The one or more hardware processors are further configured to obtain care consultant information associated with a plurality of care consultants associated with the call center including first care consultant information associated with a first care consultant. The first care consultant information includes care consultant profile information associated with the first care consultant. The first care consultant information includes care consultant conversation characteristics associated with the first care consultant during a current conversation or a past conversation. The first care consultant information includes care consultant previous session information associated with the first care consultant. The first care consultant information includes care consultant real-time physiological state information associated with the first care consultant. The first care consultant information includes care consultant current working conditions information associated with the first care consultant. The one or more hardware processors are further configured to analyze the first subject information and the first care consultant information to determine whether a match exists between the first subject and the first care consultant.

It is yet another aspect of one or more embodiments of the present disclosure to provide a method configured for matching subjects that call into a call center where calls are answered by care consultants that provide health care or consult on health care remotely via the call center. Matching is based on holistic information related to both the individual subjects and the individual care consultants. The method comprises one or more hardware processors configured to execute machine-readable instructions and/or other components. The method comprises, responsive to receiving a call from a first subject, obtaining first subject information associated with the first subject. The first subject information includes subject profile information associated with the first subject. The first subject information includes subject conversation characteristics associated with the first subject during a current conversation or a past conversation. The first subject information includes subject previous session information associated with the first subject. The first subject information includes subject real-time physiological state information associated with the first subject. The first subject information includes subject present living conditions information associated with the first subject. The method further comprises obtaining care consultant information associated with a plurality of care consultants associated with the call center including first care consultant information associated with a first care consultant. The first care consultant information includes care consultant profile information associated with the first care consultant. The first care consultant information includes care consultant conversation characteristics associated with the first care consultant during a current conversation or a past conversation. The first care consultant information includes care consultant previous session information associated with the first care consultant. The first care consultant information includes care consultant real-time physiological state information associated with the first care consultant. The first care consultant information includes care consultant current working conditions information associated with the first care consultant. The method further comprises analyzing the first subject information and the first care consultant information to determine whether a match exists between the first subject and the first care consultant.

It is yet another aspect of one or more embodiments of the present disclosure to provide a system configured for matching subjects that call into a call center where calls are answered by care consultants that provide health care or consult on health care remotely via the call center. Matching is based on holistic information related to both the individual subjects and the individual care consultants. The system comprises, responsive to receiving a call from a first subject, means for obtaining first subject information associated with the first subject. The first subject information includes subject profile information associated with the first subject. The first subject information includes subject conversation characteristics associated with the first subject during a current conversation or a past conversation. The first subject information includes subject previous session information associated with the first subject. The first subject information includes subject real-time physiological state information associated with the first subject. The first subject information includes subject present living conditions information associated with the first subject. The system further comprises means for obtaining care consultant information associated with a plurality of care consultants associated with the call center including first care consultant information associated with a first care consultant. The first care consultant information includes care consultant profile information associated with the first care consultant. The first care consultant information includes care consultant conversation characteristics associated with the first care consultant during a current conversation or a past conversation. The first care consultant information includes care consultant previous session information associated with the first care consultant. The first care consultant information includes care consultant real-time physiological state information associated with the first care consultant. The first care consultant information includes care consultant current working conditions information associated with the first care consultant. The system further comprises means for analyzing the first subject information and the first care consultant information to determine whether a match exists between the first subject and the first care consultant.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Telenursing refers to the use of telecommunications and information technology in the provision of nursing services between a subject and a care consultant, or between a plurality of care consultants. Telenursing is often provided from a call center and includes the delivery, management, and/or coordination of care and services provided via telecommunications technology within the domain of nursing. Telenursing includes the use of telecommunications technology in nursing to enhance subject care. Remote communication such as "calls" refers to any telecommunications technology facilitating communication over a distance by cable, telegraph, telephone, network, broadcasting, and/or other transmission, emission or reception of signs, signals, writings, images, sounds, or intelligence of any nature by wire, radio, optical or other electromagnetic systems. Telecommunications answered by care consultants that provide health care or consult on health care remotely via the call center include telephone calling, video calling, videotelephony, virtual reality environmental calls, holograms, webcam, videophone, videoconferencing, telepresence, voice over Internet Protocol (VoIP), and/or other methods of remote communication. A call center is a physical place where subject and other telephone calls are handled by an organization, usually with some amount of machine automation. A care consultant may include one or more of a nurse, doctor, caregiver, care provider, health professional, mental health professional, heath care practitioner, physician, dentist, pharmacist, physician assistant, advanced practice registered nurse, surgeon, surgeon's assistant, athletic trainer, surgical technologist, midwife, dietitian, therapist, psychologist, chiropractor, clinical officer, social worker, phlebotomist, occupational therapist, physical therapist, radiographer, radiotherapist, respiratory therapist, audiologist, speech pathologist, optometrist, operating department practitioner, emergency medical technician, paramedic, medical laboratory scientist, medical prosthetic technician, and/or other human resources trained to provide some type of health care service.

As a field, telenursing is part of telehealth, and has many points of contacts with other medical and non-medical applications, such as tele-diagnosis, teleconsultation, telemonitoring, e-health (healthcare practice supported by electronic processes and communication), m-health (mobile health, the practice of medicine and public health supported by mobile devices), e-coaching (coaching which uses information and communication technology), Philips Health Suite Digital Platform, and/or other applications. Telehealth methods include one or more of real-time telephone-based, web-consults (e.g., two way audio and video), peripheral devices (e.g., blood pressure, scales, glucose monitoring, EKG/cardiac monitoring, dermascope, otoscopes, pedometers, and/or other peripheral devices), images, audio, video, any combination of the preceding, and/or other methods. Telehealth equipment includes phone lines, internet, phone, computer, camera, microphone, cell phones, equipment related to Philips Lifeline, sensor technology, peripheral devices, and/or other equipment.

Care consultants should be able to work independently, make decisions about the caller's need for further care, give advice on self-care, or refer the caller to the appropriate source of help. When telecare consultants triage callers' conditions, their assessments are based on verbal communication. This demands a high level of communication skills and the ability to listen. Subjects can connect with care consultants through a variety of communication channels including internet, 4G, smart phones, and/or other communication mediums. These and other technologies can provide care consultants with additional tools to better assist calling subjects. Care consultants can monitor subject's physiological parameters via sensors (e.g., wearable sensors, blood pressure, Philips Health watch, Apple watch, and/or other sensors), and data platforms (e.g., Philips Health Suite digital platform). Still, the primary resource of care consultants is their level of communication with and empathy of their subject. Some people "click" with each other in that they communicate effortlessly and understand each other well. This can happen due to various reasons such as common cultural values, common understanding, ability to reason and listen, and/or other reasons.

There is a clear need to reform remote care systems for reasons of cost and outreach. By making sure that the care consultant has all tools, information, and professional support to assist the subject, support provided by the care consultant will be of higher quality, which in turn will improve the job and personal satisfaction of the care consultant. The present disclosure comprises a system and method for matching the physiological and psychological states and profiles of subjects who need telenursing with the care consultant best equipped to assist them in order to maximize the effectiveness of care and minimize the stress (both short term and long term) to the care consultants. In some embodiments, wearable and remote sensors infer the states and profiles of both subjects and care consultants. Matching subjects with care consultants may be facilitated using historical and live data. The physiological and psychological state of the care consultant is highly likely to influence the quality of communication and support they can provide to the subject. As used herein, the term "physiological" encompasses "psychological", however, for purposes of brevity, "psychological states" may not always be stated. In order to prevent or alleviate the undesired effects of existing call center routing techniques for determining the selection of a call center consultant, the present disclosure facilitates matching subjects that call into a call center with care consultants that can assist the subject in the best manner.

Figure 1:
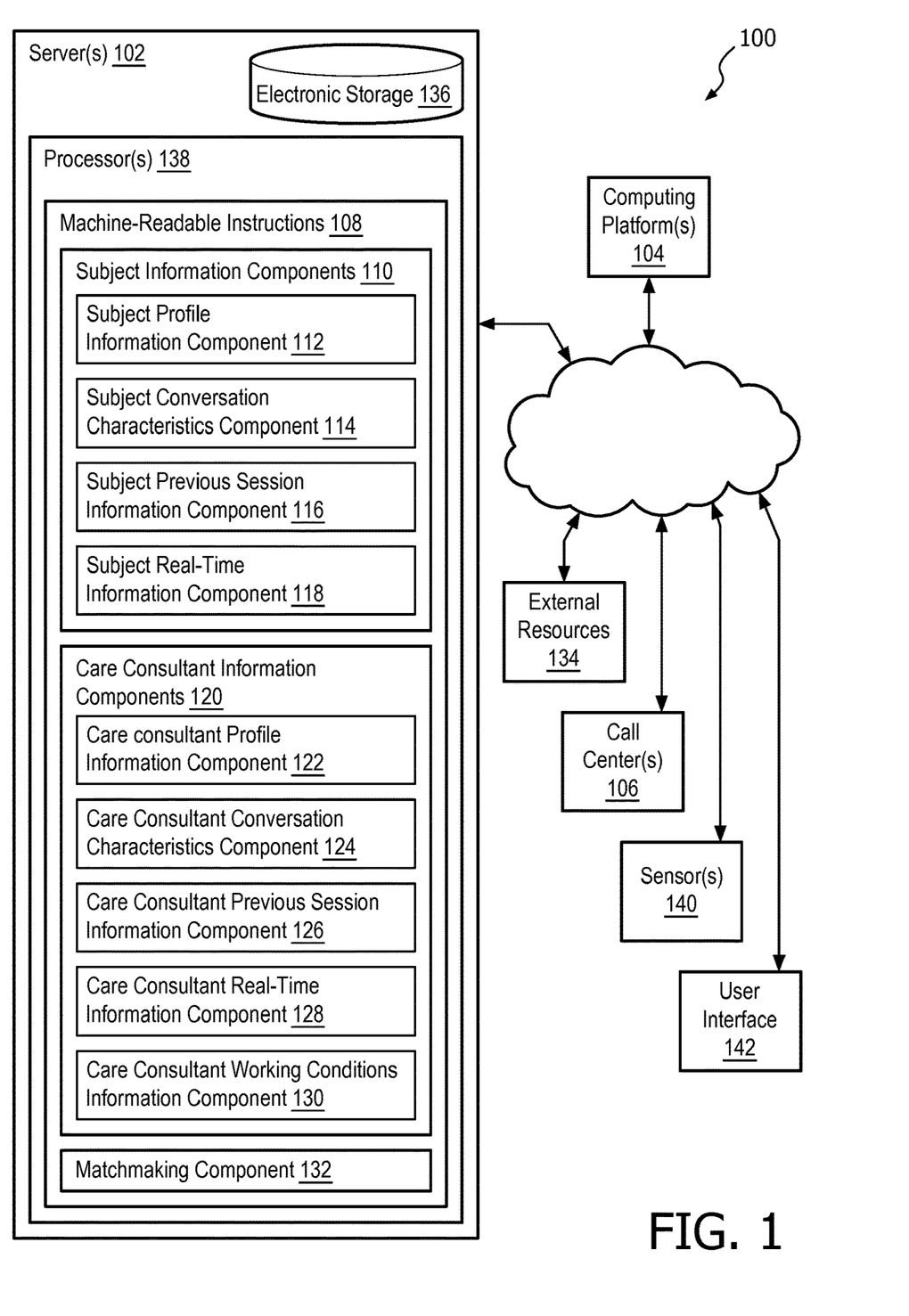
FIG. 1 illustrates a system configured for matching subjects that call into a call center where calls are answered by care consultants that provide care or consult on care remotely via the call center, wherein the matching is based on holistic information related to both the individual subjects and the individual care consultants, in accordance with one or more embodiments.

FIG. 1 illustrates a system 100 configured for matching subjects that call into a call center 106 where calls are answered by care consultants that provide care or consult on care remotely via call center 106, wherein the matching is based on holistic information related to both the individual subjects and the individual care consultants, in accordance with one or more embodiments. In some embodiments, one or more characteristics of the holistic information of the subject and/or one or more characteristics of the holistic information of the care consultant may be weighted such that matching the subject with the care consultant is determined based on the weighted characteristics. In some embodiments, one or more parameters that are most critical to facilitate the best conversation at a given time will receive higher weights and will have a higher impact on how the match is performed.

In some embodiments, system 100 may include one or more servers 102. Server(s) 102 may be configured to communicate with one or more computing platforms 104 according to a client/server architecture, a peer-to-peer architecture, and/or other architectures. Server(s) 102 may be configured to execute machine-readable instructions 108. Machine-readable instructions 108 may include one or more of subject information components 110, care consultant information components 120, a matchmaking component 132, and/or other machine-readable instruction components. The subject information components 110 may include one or more of a subject profile information component 112, a subject conversation characteristics component 114, a subject previous session information component 116, a subject real-time information component 118, a subject present living conditions information component 119, and/or other machine-readable instruction components. The care consultant information components 120 may include one or more of a care consultant profile information component 122, a care consultant conversation characteristics component 124, a care consultant previous session information component 126, a care consultant real-time information component 128, a care consultant working conditions information component 130, and/or other machine-readable instruction components.

In some embodiments, responsive to receiving a call from a first subject, subject information components 110 are configured to obtain first subject information associated with the first subject. The first subject information includes subject profile information associated with the first subject. In some embodiments, subject profile information component 112 may be configured to provide subject profile information associated with the first subject. The subject profile information includes one or more of demographic information of the first subject, medical history of the first subject, location of the first subject, cultural background of the first subject, recreational interests of the first subject, and/or other subject profile information.

In some embodiments, the first subject information may include subject conversation characteristics associated with the first subject during a current conversation or a past conversation. In some embodiments, subject conversation characteristics component 114 may be configured to provide subject conversation characteristics associated with the first subject. The subject conversation characteristics include one or more of speech tempo, pitch, loudness, vocabulary, ease of articulation, listening ability, hearing problems, language, expressions used, and/or other subject conversation characteristics. For example, a subject's speech characteristics can change with age and with the onset of disease. Elderly subjects, in general, talk slowly, softly, with limited dynamic range of pitch, often use limited vocabulary, can have a coarse voice, articulation problems, and/or other challenging conversation characteristics. Communication with subjects having certain conditions, such as Parkinson's disease, can be an even greater challenge. Many individuals with Parkinson's disease will have speech and voice disorders at some time in the course of their disease. The most common perceptual speech characteristics include reduced loudness, mono pitch, hoarseness, a breathy voice quality, imprecise articulation, and/or other speech characteristics. These speech symptoms may be related to the rigidity of movement, slowness of movement, and reduced amplitude of movement of individuals with Parkinson's disease. As another consideration, subjects with Parkinson's disease may not be aware that they are getting softer in their speech and more difficult to understand. In addition, elderly subjects can have hearing problems and may not be able to hear certain frequencies or voices that are not loud enough. Moreover, they may have cognition problems and may not be able to follow and comprehend instructions. For these and other considerations, the present disclosure may match the subject to the care consultant based on the aforementioned speech and conversation parameters.

In some embodiments, the first subject information may include subject previous session information associated with the first subject. In some embodiments, subject previous session information component 116 may be configured to provide subject previous session information associated with the first subject. The subject previous session information relates to past assistance received by the first subject via the call center including corresponding care consultant information and/or other subject previous session information. For example, information such as which care consultant did the subject speak with and for how long, was the subject assisted properly, did the subject become angry or stressed, was the subject satisfied or dissatisfied, and/or other previous session information may be obtained indirectly or directly from the subject.

In some embodiments, the first subject information may include subject real-time physiological state information associated with the first subject. In some embodiments, subject real-time information component 118 may be configured to provide subject real-time information associated with the first subject. In some embodiments, the term "real-time" may refer to "near real-time." However, for purposes of brevity, "near real-time" will not always be stated. The subject real-time physiological state information includes one or more of heart rate of the first subject, electrodermal activity of the first subject, blood pressure of the first subject, body temperature of the first subject, pulse rate of the first subject, respiration rate of the first subject, blood sugar level of the first subject, heart rate variability of the first subject, skin temperature of the first subject, skin conductance response of the first subject, activity data of the first subject, movement of the first subject, and/or other real-time physiological state information. In some embodiments, home test tools may provide additional subject real-time physiological state information, including one or more of blood test information of the first subject, cholesterol of the first subject, hormone information of the first subject, electroencephalogram (EEG) (i.e., brain activity) of the first subject, electromyogram (EMG) (i.e., muscle activity) of the first subject, electrocardiogram (ECG or EKG) (i.e., heart activity) of the first subject, strength of the first subject, stamina of the first subject, grip strength of the first subject, gain and balance related information of the first subject, and/or other real-time physiological state information. Subject real-time physiological state information may be monitored using sensors such as vital signs sensors (e.g., Philips Vital Signs Camera and/or other vital signs equipment), sound and video recorders, cameras, floor sensors (e.g., smart floors), wearable sensors (e.g., smart watch, Philips Lifeline pendant, and/or other sensors), in-body sensors (e.g., electronic pills that are swallowed), and/or other physiological state monitors. In some embodiments, facial expressions can be assessed to determine mood, emotion, pain, tiredness, and/or other real-time physiological state information of the first subject. In some embodiments, image processing can be used to detect of there is any asymmetry on the face of the subject, eye pupil size and movement analysis, analysis of the veins in the eye, and/or other real-time physiological state information of the first subject. An exemplary subject sensor configuration is provided in connection with FIG. 2.

In some embodiments, the first subject information includes subject present living conditions information associated with the first subject. In some embodiments, subject present living conditions information component 119 may be configured to provide subject present living conditions information associated with the first subject. In some embodiments, the subject present living conditions information includes subject location information associated with the first subject. The subject location information may include one or more of geographical information, physical address information, caller ID (caller identification, CID) information, Global Positioning System (GPS) information, local area wireless computer networking (Wi-Fi or WiFi) information, wireless local area network (WLAN) information, wireless network access point (hotspot) information, Internet Protocol address (IP address), network address information, and/or other identification and/or location addressing information.

In some embodiments, the subject present living conditions information includes subject environmental information associated with the first subject. The subject environmental information may include one or more of subject present living conditions, subject current surroundings, is the subject at their home or at a location other than their home, is the subject in a car or other transport, current activity of the subject, is the subject alone or accompanied, if accompanied then by whom, is the subject in a public location or private location, is the subject indoors or outdoors, what supplies does the subject have access to, and/or other environmental information.

In some embodiments, the subject present living conditions information includes subject device and sensor availability information associated with the first subject. The subject device and sensor availability information may include one or more of does the subject have access to devices such as medical diagnostic equipment and/or sensors, what devices and/or technical equipment is available to the subject, what sensors are available to the subject, what device and/or sensor information is configured to be received by the care consultant and/or call center, what device and/or sensor information is configured to be received by the subject, are the available devices and/or sensors functioning properly, and/or other subject device and sensor availability information.

In some embodiments, care consultant information component 120 is configured to obtain care consultant information associated with a plurality of care consultants associated with the call center including first care consultant information associated with a first care consultant. The first care consultant information includes care consultant profile information associated with the first care consultant. In some embodiments, care consultant profile information component 122 may be configured to provide care consultant profile information associated with a first care consultant. The care consultant profile information includes one or more of education of the first care consultant, experience of the first care consultant, expertise of the first care consultant, technical knowledge of the first care consultant, cultural background of the first care consultant, recreational interests of the first care consultant, and/or other care consultant profile information. For example, if the subject is a health failure subject with high blood pressure, care consultants having technical or medical expertise with such diseases may be assigned a higher priority weight. In another example, a subject's interest in football may be weighted such that the subject is matched with a care consultant who has an interest in football. Moreover, a subject's cultural background may be weighted such that the subject is matched with a care consultant with a similar cultural background (e.g., speaking the same dialect, coming from the same region, living in the same region, having the same religion, and/or other backgrounds). By establishing a subject-care consultant match based on social, cultural, and/or other corresponding characteristics, more honest and open communication between the subject and care consultant may occur. In some embodiments, social profiles (e.g., Facebook, Instagram, and/or other social profiles) of care consultants and/or subjects may be used to facilitate matching care consultants and subjects with common interests and/or hobbies.

In some embodiments, the first care consultant information may include care consultant conversation characteristics associated with the first care consultant during a current conversation or a past conversation. In some embodiments, care consultant conversation characteristics component 124 may be configured to provide care consultant conversation characteristics associated with a first care consultant. The care consultant conversation characteristics include one or more of speaking tempo, pitch, loudness, vocabulary, turn taking, listening ability, language, expressions used, and/or other care consultant conversation characteristics. For example, conversation characteristics of an elderly subject who speaks slowly may be weighted such that the subject is matched with a care consultant who mimics the subject's speech tempo, whose pitch of voice is not distracting and easier to hear, who can listen and understand distorted speech, and/or other corresponding characteristics.

In some embodiments, the first care consultant information may include care consultant previous session information associated with the first care consultant. In some embodiments, care consultant previous session information component 126 may be configured to provide care consultant previous session information associated with a first care consultant. The care consultant previous session information relates to individual subjects assisted by the first care consultant, types of assistance provided by the first care consultant, and/or other previous session information. In addition, characteristics of the last call (e.g., length, difficulty, content, and/or other characteristics) that the care consultant engaged in may be taken into account. In some embodiments, empathic care consultants may be profiled by system 100 by detecting increased care consultant stress only at the early part of remote sessions, but the resulting evaluation of the remote session being positively rated by both parties. Subsequently, the level of empathy and/or caring required for the subject can be matched up whilst preventing too much sustained stress on such care consultants. Similarly, non-empathic care consultants may be profiled by the brevity of their remote sessions with relatively low stress consistently from beginning to end.

In some embodiments, the first care consultant information may include care consultant real-time physiological state information associated with the first care consultant. In some embodiments, the term "real-time" may refer to "near real-time." However, for purposes of brevity, "near real-time" will not always be stated. In some embodiments, care consultant real-time information component 128 may be configured to provide care consultant real-time information associated with a first care consultant. The care consultant real-time physiological state information includes one or more of tiredness of the first care consultant, stress level of the first care consultant, speech of the first care consultant, facial expressions of the first care consultant, posture of the first care consultant, computer usage of the first care consultant, eye movements of the first care consultant, blood vessels in eye of the first care consultant, eating behavior of the first care consultant, and/or other real-time physiological state information. Psychological and/or physiological state information may be inferred from objective measurements and/or may be assessed based on questionnaires completed by care consultants after each call. The questionnaires may be validated questionnaires for psychological and/or physiological state monitoring. For example, a slowly speaking subject that cannot hear well may be weighted such that the subject is not matched with a care consultant who is exhibiting real-time physiological state characteristics such as tiredness, stress, anger, impatience, and/or other conflicting characteristics.

In some embodiments, the first care consultant information may include care consultant current working conditions information associated with the first care consultant. In some embodiments, care consultant working conditions information component 130 may be configured to provide care consultant current working conditions information associated with a first care consultant. The care consultant current working conditions information includes one or more of number of hours worked by the first care consultant, availability of other care consultants, communication between the first care consultant and other care consultants and doctors, technical equipment accessible to the first care consultant (e.g., devices to visualize and interpret incoming subject data), location of the call center in which the first care consultant is working, duration of previous call engaged by the first care consultant, interval since previous call engaged by the first care consultant, availability of the first care consultant, and/or other current working conditions information. For example, critical subjects, which may have a complex condition that requires immediate professional attention (e.g., a subject that has just fallen and has a fractured bone) may be weighted such that the subject is matched with a care consultant who is immediately available and is in communication with emergency medical technicians.

In some embodiments, care consultant current working conditions information may also include availability of devices to visualize and interpret incoming subject information. In some embodiments, system 100 may be configured to route calls to care consultants working from home, at another office, and/or at other remote locations outside the call center. In cases where the care consultant may be working remotely, assistive tools (e.g., medical database, display screens, diagnostic equipment, and/or other tools) accessible to the care consultant may be limited. For example, a care consultant that does not have access to technical equipment may be weighted with less priority such that the subject is matched with the care consultant who can monitor the subject's real-time physiological state information. In addition, if the subject has collected sensor data and/or possesses measurement equipment configured for use during the subject-care consultant interaction, care consultants having tools to visualize and interpret such data are preferred and may be weighted with higher priority. For example, care consultants having access to the screen displaying the incoming data from the subject are given higher priority (i.e., weighted higher) for matchmaking with that subject.

In some embodiments, care consultants that are currently unavailable or assisting other subjects can be considered for subject-care consultant matchmaking. For example, if it is determined that the best matching care consultant is currently unavailable, but will soon be available, the subject may be instructed to wait instead of immediately connecting the subject to an available, but less matching, care consultant. As another example, for subjects that do not have a critical condition, and/or are calling for their regular conversation, it may be preferred that they are connected with the care consultant that they are familiar and happy with. In some embodiments, system 100 may be configured for predictive analytics. Predictive analytics may facilitate maintaining the availability of an available care consultant based on the expectation of receiving a call from a matching subject. For example, if the data shows (expected or predicted) that the subject A will call on Friday afternoon around 3*pm* (due to scheduled call, drug intake, test that needs to be performed, and/or other reasons), it may be preferable to keep the best matching care consultant available around 3*pm* (e.g., from 2:50*pm* to 3:10*pm*) to ensure that when the subject calls, they may be immediately connected to the matching care consultant.

In some embodiments, care consultant working conditions may be improved by preventing the care consultant from getting exhausted, annoyed, stressed, and/or other negative dispositions. Care consultant's working conditions may be weighted such that sufficient recovery time from a previous call is allotted. For example, a care consultant that has been engaged with a subject for an extended period may be weighted with less priority such that the subject is matched with a care consultant who is re-energized and/or has not recently completed a subject call. First care consultant information is analyzed to determine if a threshold level of first care consultant working conditions are being met. In some embodiments, the physiological and psychological state of care consultants in the call center may be continuously monitored during working hours. The physiological state of care consultants may be monitored unobtrusively using wearable sensors, environmental sensors (e.g., vital signs camera, speech and video analysis, pressure sensors in chair, use of keyboard and mouse, mistakes when typing, and/or other sensors), and/or other physiological state monitors. An exemplary care consultant sensor configuration is provided in connection with FIG. 2.

In some embodiments, matchmaking component 132 is configured to analyze the first subject information and the first care consultant information to determine whether a subject-care consultant match exists between the first subject and the first care consultant. In some embodiments, matchmaking component 132 may be matchmaking software configured to receive features of one or more care consultants and features of the subject as input and determine the care consultant who may assist the subject the best based on the received subject and care consultant data. In some embodiments, the matchmaking software may be data-based optimization tools configured to facilitate data mining algorithms and/or hand-crafted rules.

In some embodiments, interactions between the first subject and the first care consultant may be analyzed to determine a level of quality of communication. Quality of communication may be determined by obtaining quantitative measurements from the first subject and the first care consultant. The quality of communication information may be stored for use in subsequent subject-care consultant matchmaking. The quality of communication may be determined in real-time or near real-time to facilitate subject-care consultant matchmaking. The quality of communication may be determined by analyzing interactions between the first subject and the first care consultant. Assessing the quality of communication may include receiving feedback from the first subject, either directly (e.g., via a survey, questionnaire, and/or other direct feedback) or indirectly (e.g., via physiological state monitoring and/or other indirect feedback). The subject-care consultant matchmaking may be adapted, accordingly, based on the quality of communication assessment not reaching an acceptable level. In some embodiments, responsive to the quality of communication of the first subject and the first care consultant not meeting a threshold level of quality of communication, interaction between the first subject and a second care consultant may be facilitated.

In some embodiments, system 100 may comprise a database of available care consultants for one or more call centers. The database of available care consultants may include static information (e.g., biographical information, profile information, past communication summaries, geographical location, and/or other previously collected data) and/or dynamic information (e.g., information being received in real-time or near real-time including physiological state of the care consultant (such as tiredness and stress level), information about current working conditions (such as how many hours worked, what devices and/or resources are available, located at home or at workplace, and/or other current working conditions). In some embodiments, system 100 may comprise a database of care consultants at one or more call centers that are currently assisting other subjects.

In some embodiments, system 100 may comprise a database of subject information. The database of subject information may include static subject information, (e.g., biographical information, medical information, health history, profile information, past communication summaries, geographical location, other non-health related information, and/or other previously collected data) and/or dynamic subject information (e.g., information being received in real-time or near real-time about the condition of the subject, provided by the subject and/or obtained from sensor data, measurement equipment, or other technical equipment). In some embodiments, system 100 may comprise a database of subjects registered with a particular call center.

In some embodiments, system 100 may comprise a plurality of call centers. System 100 may be configured to obtain location information from the caller and direct the call to the nearest available call center. In some embodiments, system 100 may be configured to prioritize the best matching care consultant in a secondary call center over a nearer, but less matching care consultant.

In some embodiments, system 100 may comprise one or more sensors 140. Sensor(s) 140 may include one or more of peripheral devices, wearable sensors, vital signs sensors, environmental sensors, and/or other sensors. Peripheral devices may include one or more of blood pressure sensors, scales, glucose monitors, EKG/cardiac monitors, dermascopes, otoscopes, pedometers, and/or other peripheral device sensors. Wearable sensors may include one or more of smart watch, Philips Lifeline pendant, Philips Health watch, Apple watch, and/or other sensors. Vital signs sensors may include one or more of a Philips Vital Signs Camera, sound and video recorders, and/or other vital signs equipment. Environmental sensors may include one or more of vital signs sensors, speech sensors, pressure sensors in chair, sensors configured to monitor use of keyboard and mouse, sensors configured to monitor mistakes while typing, and/or other sensors.

In some embodiments, user interface 142 is configured to provide an interface between system 100 and user(s) (e.g., subjects, care consultants, and/or other users) through which user(s) may provide information to and receive information from system 100. This enables data, results, and/or instructions and any other communicable items, collectively referred to as "information," to be communicated between the user(s) and one or more of processor(s) 138, and/or electronic storage 136. Examples of interface devices suitable for inclusion in user interface 142 include a keypad, buttons, switches, a keyboard, knobs, levers, a display screen, a touch screen, speakers, a microphone, an indicator light, an audible alarm, and a printer. It is to be understood that other communication techniques, either hard-wired or wireless, are also contemplated by the present invention as user interface 142. For example, the present invention contemplates that user interface 142 may be integrated with a removable storage interface provided by electronic storage 136. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 142 include, but are not limited to, an RS-232 port, RF link, an IR link, modem (telephone, cable or other). In short, any technique for communicating information with system 100 is contemplated by the present invention as user interface 142.

In some embodiments, server(s) 102, computing platform (s) 104, call center(s) 106, external resources 134, sensor(s) 140, and/or user interface 142 may be operatively linked via one or more electronic communication links. For example, such electronic communication links may be established, at least in part, via a network such as the Internet and/or other networks. It will be appreciated that this is not intended to be limiting, and that the scope of this disclosure includes embodiments in which server(s) 102, computing platform(s) 104, call center(s) 106, external resources 134, sensor(s) 140, and/or user interface 142 may be operatively linked via some other communication media.

A given computing platform 104 may include one or more processors configured to execute machine-readable instructions 108. The machine-readable instructions may be configured to enable an expert or user associated with the given computing platform 104 to interface with system 100, call center(s) 106, external resources 134, and/or sensor(s) 140, and/or provide other functionality attributed herein to computing platform(s) 104. By way of non-limiting example, the given computing platform 104 may include one or more of a desktop computer, a laptop computer, a handheld computer, a tablet computing platform, a NetBook, a Smartphone, a gaming console, and/or other computing platforms.

External resources 134 may include sources of information, hosts and/or providers of electronic health records (EHRs), external entities participating with system 100, and/or other resources. In some embodiments, some or all of the functionality attributed herein to external resources 100 may be provided by resources included in system 100.

Server(s) 102 may include electronic storage 136, one or more processors 138, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 136 may comprise non-transitory storage media that electronically stores information. The electronic storage media of electronic storage 136 may include one or both of system storage that is provided integrally (i.e., substantially non-removable) with server(s) 102 and/or removable storage that is removably connectable to server(s) 102 via, for example, a port (e.g., a USB port, a firewire port, and/or other types of ports) or a drive (e.g., a disk drive and/or other types of drive). Electronic storage 136 may include one or more of optically readable storage media (e.g., optical disks and/or other optically readable storage media), magnetically readable storage media (e.g., magnetic tape, magnetic hard drive, floppy drive, and/or other magnetically readable storage media), electrical charge-based storage media (e.g., EEPROM, RAM, and/or other electrical charge-based storage media), solid-state storage media (e.g., flash drive, and/or other solid-state storage media), and/or other electronically readable storage media. Electronic storage 136 may include one or more virtual storage resources (e.g., cloud storage, a virtual private network, and/or other virtual storage resources). Electronic storage 136 may store software algorithms, information determined by processor (s) 138, information received from server(s) 102, information received from computing platform(s) 104, and/or other information that enables server(s) 102 to function as described herein.

Processor(s) 138 may be configured to provide information processing capabilities in server(s) 102. As such, processor(s) 138 may include one or more of a digital processor, an analog processor, a digital circuit designed to process information, an analog circuit designed to process information, a state machine, and/or other mechanisms for electronically processing information. Although processor(s) 138 is shown in FIG. 1 as a single entity, this is for illustrative purposes only. In some embodiments, processor(s) 138 may include a plurality of processing units. These processing units may be physically located within the same device, or processor(s) 138 may represent processing functionality of a plurality of devices operating in coordination. The processor(s) 138 may be configured to execute machine-readable instruction components 110, 112, 114, 116, 118, 119, 120, 122, 124, 126, 128, 130, 132, and/or other machine-readable instruction components. Processor(s) 138 may be configured to execute machine-readable instruction components 110, 112, 114, 116, 118, 119, 120, 122, 124, 126, 128, 130, 132, and/or other machine-readable instruction components by software; hardware; firmware; some combination of software, hardware, and/or firmware; and/or other mechanisms for configuring processing capabilities on processor(s) 138. As used herein, the term "machine-readable instruction component" may refer to any component or set of components that perform the functionality attributed to the machine-readable instruction component. This may include one or more physical processors during execution of processor readable instructions, the processor readable instructions, circuitry, hardware, storage media, or any other components.

It should be appreciated that although machine-readable instruction components 110, 112, 114, 116, 118, 119, 120, 122, 124, 126, 128, 130, and 132 are illustrated in FIG. 1 as being implemented within a single processing unit, in embodiments in which processor(s) 138 includes multiple processing units, one or more of machine-readable instruction components 110, 112, 114, 116, 118, 119, 120, 122, 124, 126, 128, 130, and/or 132 may be implemented remotely from the other machine-readable instruction components. The description of the functionality provided by the different machine-readable instruction components 110, 112, 114, 116, 118, 119, 120, 122, 124, 126, 128, 130, and/or 132 described below is for illustrative purposes, and is not intended to be limiting, as any of machine-readable instruction components 110, 112, 114, 116, 118, 119, 120, 122, 124, 126, 128, 130, and/or 132 may provide more or less functionality than is described. For example, one or more of machine-readable instruction components 110, 112, 114, 116, 118, 119, 120, 122, 124, 126, 128, 130, and/or 132 may be eliminated, and some or all of its functionality may be provided by other ones of machine-readable instruction components 110, 112, 114, 116, 118, 119, 120, 122, 124, 126, 128, 130, and/or 132. As another example, processor(s) 138 may be configured to execute one or more additional machine-readable instruction components that may perform some or all of the functionality attributed below to one of machine-readable instruction components 110, 112, 114, 116, 118, 119, 120, 122, 124, 126, 128, 130, and/or 132.

Figure 2:
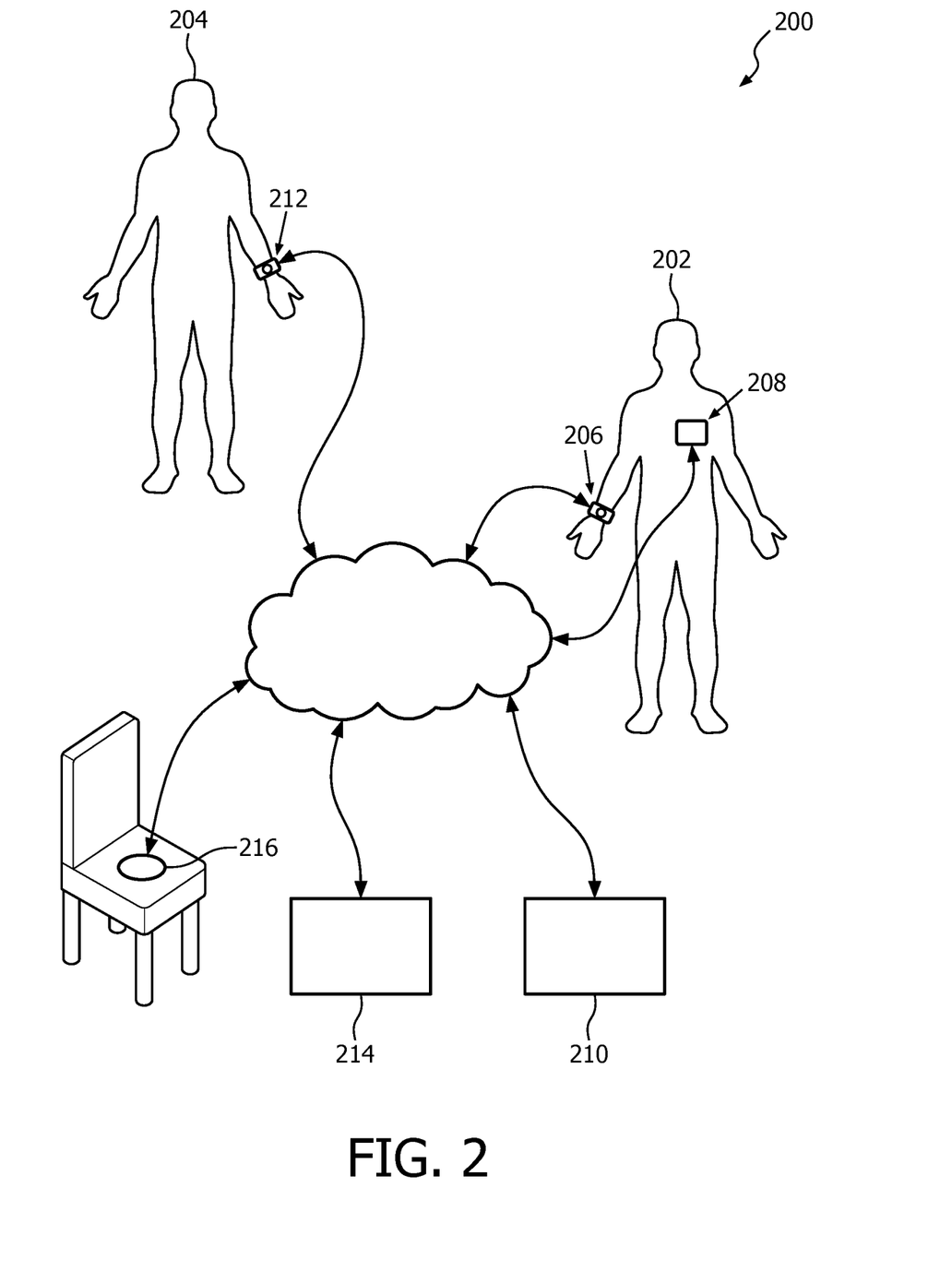
FIG. 2 illustrates an exemplary sensor configuration, in accordance with one or more embodiments.

FIG. 2 illustrates an exemplary sensor configuration 200, in accordance with one or more embodiments. In some embodiments, a subject 202 may have subject real-time physiological state information and/or other subject information monitored by sensors configured to provide output signals that convey information related to the real-time physiological state information of subject 202 and/or other information about the condition of subject 202. In some embodiments, a care consultant 204 may have care consultant real-time physiological state information and/or care consultant current working conditions information obtained by sensors configured to provide output signals that convey information related to the real-time physiological state information of care consultant 204, current working conditions information of care consultant 204, and/or other information about care consultant 204. Sensor configuration 200 may include one or more of subject wearable sensors 206, subject physiological state monitors 208, subject vital signs sensors 210, care consultant wearable sensors 212, care consultant environmental sensors 214, pressure sensors 216, and/or other sensors, in accordance with one or more embodiments. Subject wearable sensors 206 may include one or more of smart watch, Philips Lifeline pendant, Philips Health watch, Apple watch, and/or other wearable sensors. Subject physiological state monitors 208 may include one or more of blood pressure sensors, scales, glucose monitors, EKG/cardiac monitors, dermascopes, otoscopes, pedometers, and/or other physiological state monitoring sensors. Subject vital signs sensors 210 may include one or more of a Philips Vital Signs Camera, sound and video recorders, and/or other vital signs equipment. Care consultant wearable sensors 212 may include one or more of smart watch, Philips Lifeline pendant, Philips Health watch, Apple watch, and/or other wearable sensors. Care consultant environmental sensors 214 may include one or more of vital signs sensors, speech sensors, pressure sensors in chair (e.g., pressure sensors 216), sensors configured to monitor use of keyboard and mouse, sensors configured to monitor mistakes while typing, and/or other sensors.

Figure 3:
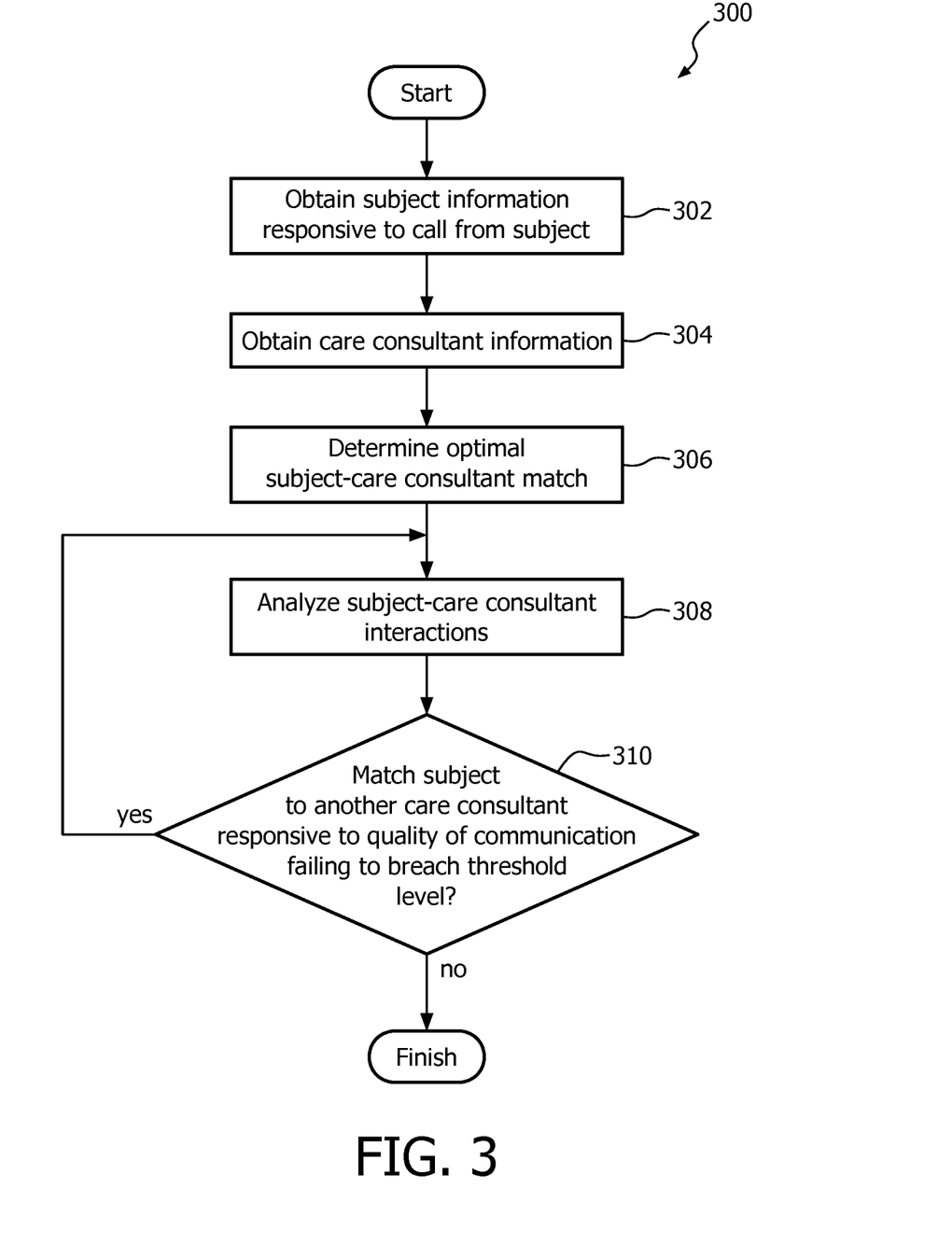
FIG. 3 illustrates a method for matching subjects that call into a call center where calls are answered by care consultants that provide care or consult on care remotely via the call center, wherein the matching is based on holistic information related to both the individual subjects and the individual care consultants, in accordance with one or more embodiments.

FIG. 3 illustrates a method 300 for matching subjects that call into a call center where calls are answered by care consultants that provide care or consult on care remotely via the call center, wherein the matching is based on holistic information related to both the individual subjects and the individual care consultants, in accordance with one or more embodiments. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, one or more operations of method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, responsive to receiving a call from a first subject, obtain first subject information associated with the first subject. In some embodiments, the first subject information comprises subject profile information associated with the first subject, subject conversation characteristics associated with the first subject during a current conversation or a past conversation, subject previous session information associated with the first subject, subject real-time physiological state information associated with the first subject, subject present living conditions information associated with the first subject, and/or other first subject information. The subject profile information includes one or more of demographic information of the first subject, medical history of the first subject, location of the first subject, cultural background of the first subject, recreational interests of the first subject, and/or other subject profile information. The subject conversation characteristics include one or more of speech tempo, pitch, loudness, vocabulary, ease of articulation, listening ability, hearing problems, language, expressions used, and/or other subject conversation characteristics. The subject previous session information relates to past assistance received by the first subject via the call center including corresponding care consultant information and/or other subject previous session information. The subject real-time physiological state information includes one or more of heart rate of the first subject, electrodermal activity of the first subject, blood pressure of the first subject, blood sugar level of the first subject, and/or other subject real-time physiological state information. The subject present living conditions information includes one or more of subject location information, subject environmental information, subject device and sensor availability information, and/or other subject present living conditions information. Operation 302 may be performed by one or more hardware processors configured to execute a machine-readable instruction component that is the same as or similar to subject information components 110 (as described in connection with FIG. 1), in accordance with one or more implementations.

At an operation 304, obtain care consultant information associated with a plurality of care consultants associated with the call center including first care consultant information associated with a first care consultant. In some embodiments, the first care consultant information comprises care consultant profile information associated with the first care consultant, care consultant conversation characteristics associated with the first care consultant during a current conversation or a past conversation, care consultant previous session information associated with the first care consultant, care consultant real-time physiological state information associated with the first care consultant, and care consultant current working conditions information associated with the first care consultant. The care consultant profile information includes one or more of education of the first care consultant, experience of the first care consultant, expertise of the first care consultant, technical knowledge of the first care consultant, cultural background of the first care consultant, recreational interests of the first care consultant, and/or other care consultant profile information. The care consultant conversation characteristics includes one or more of speaking tempo, pitch, loudness, vocabulary, turn taking, listening ability, language, expressions used, and/or other care consultant conversation characteristics. The care consultant real-time physiological state information includes one or more of tiredness of the first care consultant, stress level of the first care consultant, speech of the first care consultant, facial expressions of the first care consultant, posture of the first care consultant, computer usage of the first care consultant, eye movements of the first care consultant, blood vessels in eye of the first care consultant, eating behavior of the first care consultant, and/or other care consultant real-time physiological state information. The care consultant current working conditions information includes one or more of number of hours worked by the first care consultant, availability of other care consultants, communication between the first care consultant and other care consultants and doctors, technical equipment accessible to the first care consultant, location of the call center in which the first care consultant is working, duration of previous call engaged by the first care consultant, interval since previous call engaged by the first care consultant, availability of the first care consultant, and/or other care consultant current working conditions information. Operation 304 may be performed by one or more hardware processors configured to execute a machine-readable instruction component that is the same as or similar to care consultant information components 120 (as described in connection with FIG. 1), in accordance with one or more implementations.

At an operation 306, determine whether a subject-care consultant match exists between the first subject and the first care consultant by analyzing the first subject information and the first care consultant information. Operation 306 may be performed by one or more hardware processors configured to execute a machine-readable instruction component that is the same as or similar to matchmaking component 132 (as described in connection with FIG. 1), in accordance with one or more implementations.

At an operation 308, analyze interactions between the first subject and the first care consultant, determine a quality of communication by obtaining quantitative measurements from the first subject and the first care consultant in real-time to facilitate subject-care consultant matchmaking, adapt the subject-care consultant matchmaking accordingly. Operation 308 may be performed by one or more hardware processors configured to execute a machine-readable instruction component that is the same as or similar to matchmaking component 132 (as described in connection with FIG. 1), in accordance with one or more implementations.

At an operation 310, facilitate interaction between the first subject and a second care consultant, responsive to the quality of communication of the first subject and the first care consultant not meeting a threshold level of quality of communication. Operation 310 may be performed by one or more hardware processors configured to execute a machine-readable instruction component that is the same as or similar to matchmaking component 132 (as described in connection with FIG. 1), in accordance with one or more implementations.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured for matching subjects that call into a call center where calls are answered by care consultants that provide health care or consult on health care remotely via the call center, wherein the matching is based on holistic information related to both the individual subjects and the individual care consultants, the system comprising:

one or more hardware processors configured by machine-readable instructions to:

responsive to receiving a call from a first subject, obtain first subject information associated with the first subject, the first subject information comprising:
- subject profile information associated with the first subject,
- subject conversation characteristics associated with the first subject during a current conversation or a past conversation,
- subject previous session information associated with the first subject,
- subject real-time physiological state information associated with the first subject, and
- subject present living conditions information associated with the first subject,
  - the subject real-time physiological state information being received by the one or more hardware processors from a physiological state information sensor associated with the first subject, the physiological state information sensor configured to generate output signals indicating physiological information of the first subject;

obtain care consultant information associated with a plurality of care consultants associated with the call center including first care consultant information associated with a first care consultant, the first care consultant information comprising:
- care consultant profile information associated with the first care consultant,
- care consultant conversation characteristics associated with the first care consultant during a current conversation or a past conversation,
- care consultant previous session information associated with the first care consultant,
- care consultant real-time physiological state information associated with the first care consultant, and
- care consultant current working conditions information associated with the first care consultant, the care consultant current working conditions information comprising availability of devices to visualize and interpret the received first subject information,
  - the first care consultant information being received by the one or more hardware processors from a first care consultant sensor associated with the first care consultant, the first care consultant sensor different from the physiological state information sensor, the first care consultant sensor configured to generate output signals indicating physiological information of the first care consultant; and analyze the first subject information and the first care consultant information to determine whether a match exists between the first subject and the first care consultant.

2. The system of claim 1, wherein the one or more hardware processors are further configured by machine-readable instructions to analyze interactions between the first subject and the first care consultant to determine a quality of communication by obtaining quantitative measurements from the first subject and the first care consultant, and storing the quality of communication for use in subsequent subject-care consultant matchmaking.

3. The system of claim 2, wherein the quality of communication is determined in real-time to facilitate subject-care consultant matchmaking by analyzing interactions between the first subject and the first care consultant, assessing the quality of communication, receiving feedback from the first subject, receiving feedback from the care consultant, and adapting the subject-care consultant matchmaking accordingly.

4. The system of claim 1, wherein the one or more hardware processors are further configured by machine-readable instructions to facilitate interaction between the first subject and a second care consultant, responsive to the quality of communication of the first subject and the first care consultant not meeting a threshold level of quality of communication.

5. The system of claim 1, wherein the one or more hardware processors are further configured by machine-readable instructions to analyze the first care consultant information to determine if a threshold level of first care consultant working conditions are being met.

6. The system of claim 1, wherein the subject present living conditions information associated with the first subject comprises subject location information associated with the first subject, subject environmental information associated with the first subject, and subject device and sensor availability information associated with the first subject.

7. The system of claim 1, further incorporating the physiological state information sensor that generates the output signals.

8. The system of claim 1, further incorporating the first care consultant sensor that generates the output signals.

9. The system of claim 1, wherein the first care consultant having access to the devices comprising medical diagnostic equipment or technical equipment to visualize and interpret the first subject information is assigned a higher weight to determine matching between the first subject information and the first care consultant.

10. A method for matching subjects that call into a call center where calls are answered by care consultants that provide health care or consult on health care remotely via the call center, wherein the matching is based on holistic information related to both the individual subjects and the individual care consultants, the method being performed by one or more hardware processors configured by machine-readable instructions, the method comprising:
responsive to receiving a call from a first subject, obtaining first subject information associated with the first subject, the first subject information comprising:
- subject profile information associated with the first subject,
- subject conversation characteristics associated with the first subject during a current conversation or a past conversation,
- subject previous session information associated with the first subject, subject real-time physiological state information associated with the first subject, and
- subject present living conditions information associated with the first subject,
  - wherein the obtaining of the subject real-time physiological state information comprises receiving the subject real-time physiological state information from a physiological state information sensor associated with the first subject, the physiological state information sensor configured to generate output signals indicating physiological information of the first subject;

obtaining care consultant information associated with a plurality of care consultants associated with the call center including first care consultant information associated with a first care consultant, the first care consultant information comprising:

care consultant profile information associated with the first care consultant,
care consultant conversation characteristics associated with the first care consultant during a current conversation or a past conversation,
care consultant previous session information associated with the first care consultant,
care consultant real-time physiological state information associated with the first care consultant, and
care consultant current working conditions information associated with the first care consultant, the care consultant current working conditions information comprising availability of devices to visualize and interpret the received first subject information,
wherein the obtaining of the first care consultant information comprises receiving the first care consultant information from a first care consultant sensor associated with the first care consultant, the first care consultant sensor configured to generate output signals indicating physiological information of the first care consultant, the first care consultant sensor different from the physiological state information sensor; and
analyzing the first subject information and the first care consultant information to determine whether a match exists between the first subject and the first care consultant.

11. The method of claim 10, further comprising analyzing interactions between the first subject and the first care consultant to determine a quality of communication by obtaining quantitative measurements from the first subject and the first care consultant, and storing the quality of communication for use in subsequent subject-care consultant matchmaking.

12. The method of claim 11, further comprising determining the quality of communication in real-time to facilitate subject-care consultant matchmaking by analyzing interactions between the first subject and the first care consultant, assessing the quality of communication, receiving feedback from the first subject, receiving feedback from the care consultant, and adapting the subject-care consultant matchmaking accordingly.

13. The method of claim 10, further comprising facilitating interaction between the first subject and a second care consultant, responsive to the quality of communication of the first subject and the first care consultant not meeting a threshold level of quality of communication.

14. The method of claim 10, further comprising analyzing the first care consultant information to determine if a threshold level of first care consultant working conditions are being met.

15. The method of claim 10, wherein the subject present living conditions information associated with the first subject comprises subject location information associated with the first subject, subject environmental information associated with the first subject, and subject device and sensor availability information associated with the first subject.

16. A system configured for matching subjects that call into a call center where calls are answered by care consultants that provide health care or consult on health care remotely via the call center, wherein the matching is based on holistic information related to both the individual subjects and the individual care consultants, the system comprising:
means for, responsive to receiving a call from a first subject, obtaining first subject information associated with the first subject, the first subject information comprising:
subject profile information associated with the first subject,
subject conversation characteristics associated with the first subject during a current conversation or a past conversation,
subject previous session information associated with the first subject,
subject real-time physiological state information associated with the first subject, and
subject present living conditions information associated with the first subject,
the subject real-time physiological state information being received by the system from a physiological state information sensor associated with the first subject, the physiological state information sensor configured to generate output signals indicating physiological information of the first subject;
means for obtaining care consultant information associated with a plurality of care consultants associated with the call center including first care consultant information associated with a first care consultant, the first care consultant information comprising:
care consultant profile information associated with the first care consultant,
care consultant conversation characteristics associated with the first care consultant during a current conversation or a past conversation,
care consultant previous session information associated with the first care consultant,
care consultant real-time physiological state information associated with the first care consultant, and
care consultant current working conditions information associated with the first care consultant, the care consultant current working conditions information comprising availability of devices to visualize and interpret the received first subject information,
the first care consultant information being received by the system from a first care consultant sensor associated with the first care consultant, the first care consultant sensor different from the physiological state information sensor, the first care consultant sensor configured to generate output signals indicating physiological information of the first care consultant; and
means for analyzing the first subject information and the first care consultant information to determine whether a match exists between the first subject and the first care consultant.

17. The system of claim 16, further comprising means for analyzing interactions between the first subject and the first care consultant to determine a quality of communication by obtaining quantitative measurements from the first subject and the first care consultant, and storing the quality of communication for use in subsequent subject-care consultant matchmaking.

18. The system of claim 17, further comprising means for determining the quality of communication in real-time to facilitate subject-care consultant matchmaking by analyzing interactions between the first subject and the first care consultant, assessing the quality of communication, receiving feedback from the first subject, receiving feedback from the care consultant, and adapting the subject-care consultant matchmaking accordingly.

19. The system of claim 16, further comprising means for facilitating interaction between the first subject and a second care consultant, responsive to the quality of communication of the first subject and the first care consultant not meeting a threshold level of quality of communication.

20. The system of claim 16, further comprising means for analyzing the first care consultant information to determine if a threshold level of first care consultant working conditions are being met.

21. The system of claim 16, wherein the subject present living conditions information associated with the first subject comprises subject location information associated with the first subject, subject environmental information associated with the first subject, and subject device and sensor availability information associated with the first subject.

* * * * *